Figure 1:
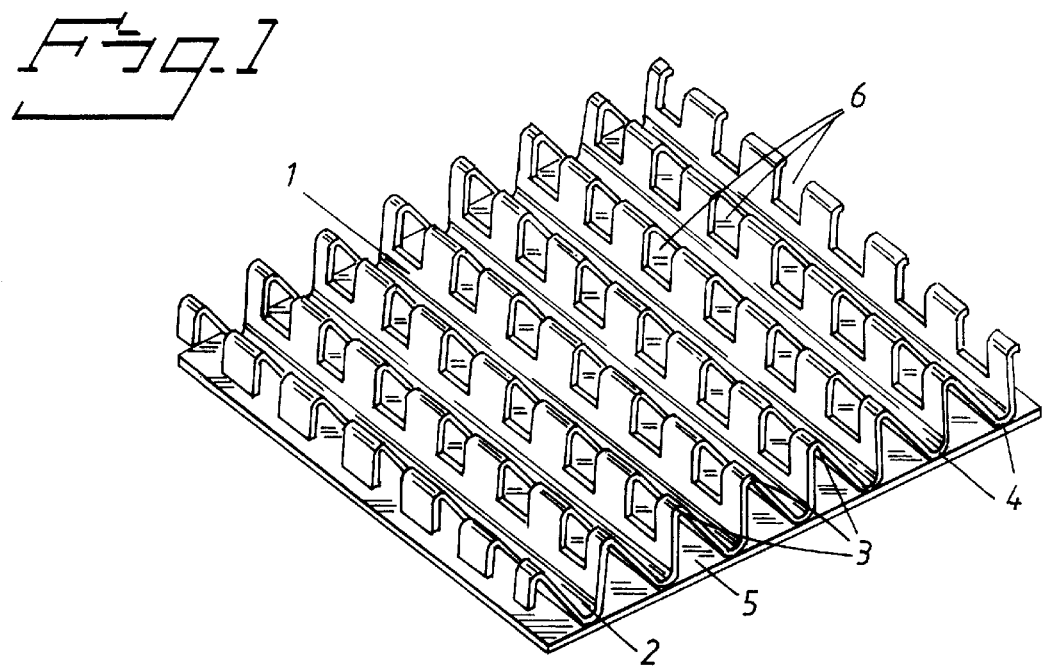

United States Patent
Hansson

[11] Patent Number: 5,976,665
[45] Date of Patent: Nov. 2, 1999

[54] LIQUID PERMEABLE CASING SHEET FOR ABSORBENT SANITARY ARTICLES

[75] Inventor: Roy Hansson, Molndal, Sweden

[73] Assignee: SCA Molnlycke AB, Gothenburg, Sweden

[21] Appl. No.: 08/835,474

[22] Filed: Apr. 8, 1997

[30] Foreign Application Priority Data

Apr. 30, 1996 [SE] Sweden ................................. 9601660

[51] Int. Cl.$^6$ ..................................................... B32B 3/10
[52] U.S. Cl. ......................... 428/136; 428/138; 428/182; 264/154; 264/259; 264/286
[58] Field of Search .................................. 428/131, 138, 428/182; 264/154, 259, 286

[56] References Cited

U.S. PATENT DOCUMENTS

| 4,389,211 | 6/1983 | Lenaghan . | |
|---|---|---|---|
| 5,114,776 | 5/1992 | Cesaroni | 428/131 |
| 5,593,755 | 1/1997 | Fuss | 428/134 |

FOREIGN PATENT DOCUMENTS

| 2 023 067A | 12/1979 | United Kingdom . |
| WO 91/11161 | 8/1991 | WIPO . |
| WO 96/00545 | 1/1996 | WIPO . |

Primary Examiner—Christopher Raimund
Attorney, Agent, or Firm—Burns, Doane, Swecker & Mathis, L.L.P.

[57] ABSTRACT

The present invention relates to a liquid-permeable casing sheet (1) for absorbent sanitary articles, such as sanitary napkins, incontinence guards and diapers. According to the invention, the casing sheet (1) includes a first layer (2) which is corrugated across at least a central part of its surface so as to provide a row of mutually parallel waves having wave crests (3) and wave troughs (4), wherein the wave crests form an article contact surface with the wearer's body when the article is in use. The casing sheet also includes rows of through-penetrating openings (6) which extend perpendicularly to the corrugations or waves and each of which opening passes through a wave crest (3). The invention also relates to a method for producing such a casing sheet.

3 Claims, 1 Drawing Sheet

U.S. Patent
Nov. 2, 1999
5,976,665

LIQUID PERMEABLE CASING SHEET FOR ABSORBENT SANITARY ARTICLES

The present invention relates to a liquid permeable casing sheet for absorbent sanitary articles, such as sanitary napkins, incontinence guards and diapers, and to a method for producing such a casing sheet.

Absorbent sanitary articles of the aforesaid kind normally comprise an absorbent core or absorbent body which is enclosed between a liquid impervious and a liquid permeable casing sheet. The liquid permeable casing sheet functions to allow liquid to pass quickly to the underlying absorbent body and to provide comfort to the wearer. In order for the sanitary article to be felt comfortable in use, it is necessary for the surface of the liquid permeable casing sheet that lies against the wearer's skin to be soft and for the wearer to feel that the article is dry. In order to achieve this feeling of dryness, it is necessary for the liquid permeable casing sheet to have good reception properties, i.e. to be capable of transporting all liquid quickly to the absorbent body, and for the article to have good rewetting properties, i.e. properties which prevent absorbed liquid from being pressed from the absorbent body and back through the casing sheet when the article is subjected to pressure.

In order to provide a dry surface against the wearer's body, the liquid permeable casing sheet normally has a hydrophobic (water repellant) or hydrophobized apertured layer which faces the wearer in use, e.g. a perforated plastic film or a plastic net or a non-woven comprised of hydrophobic or hydrophobized fibres. It is known to form the openings or apertures in recesses disposed in the layer that lies proximal to the wearer, so as to distance the absorbent body from the wearer's body and therewith obtain improved rewetting properties. It is also known to provide such recesses and openings with the intention of favouring liquid flow in a direction towards the absorbent body, such as to disfavor liquid flow in the opposite direction. One drawback with known casing sheets or layers of the aforesaid kind is that they are relatively complicated to produce and that the apertured or perforated layer is plastically deformed in conjunction with producing the recesses and openings. Another drawback is that the recesses and openings lie close to the wearer's body, therewith impeding the circulation of air within the region of the absorbent sanitary article.

An object of the present invention is to provide a liquid permeable casing sheet for absorbent sanitary articles, which has reception and rewetting properties that are at least equally as good as the earlier known casing sheet, which can be manufactured easily without plastic deformation of the layers in the casing sheet, and which in use allows air to circulate unimpeded within the area of the article in contact with the wearer's skin.

This object is achieved in accordance with the invention with a liquid permeable casing sheet for absorbent sanitary articles, such as sanitary napkins, incontinence guards and diapers, which is characterized in that the casing sheet includes a first layer which is corrugated across at least a central part of its surface such as to exhibit a row of mutually parallel wave crests and wave troughs, wherein when the article is in use the wave crests form the article contact surface with the wearer's skin and which sheet includes several rows of through-penetrating openings that extend perpendicularly to the wave crests, wherein each opening passes through a respective wave crest. As a result of the corrugated or pleated surface of such a casing sheet, the absorbent body will be spaced at a distance which improves the rewetting properties of the article. Furthermore, such a sheet will present only a small contact surface with the wearer's skin, since only the wave crests lie against the skin and the openings disposed in the wave crests enable air to circulate over the full extent of the sheet. Liquid delivered outside the openings will run down into the wave troughs and hence the sheet layer that lies proximal to the wearer will be felt to be dry very quickly after liquid has been discharged. The risk of leakage due to liquid running from the casing sheet is extremely small. The wave troughs also function as liquid reservoirs in those instances when liquid is discharged more rapidly than the rate at which the absorbent body is able to absorb the liquid, therewith reducing the spread of instantaneously discharged large quantities of liquid in comparison with a sheet having a flat contact surface.

In one preferred embodiment of the invention, the rows of openings extend at least in a central part of the first layer and preferably across the whole of said first layer. Furthermore the rows of openings have one opening in each wave crest and each opening also extends within a region of wave troughs associated with neighbouring wave crests. The first layer is made of an hydrophobic or hydrophobized material. The casing sheet will preferably include a second layer of liquid permeable material fastened to the wave troughs of the first layer.

The invention also relates to a method of producing a liquid-permeable casing sheet for absorbent sanitary articles, such as sanitary napkins, incontinence guards and diapers, said method being characterized by pleating a first layer to a corrugated form so as to obtain a row of parallel waves having wave crests and wave troughs, and thereafter providing in the first layer a plurality of rows of through-penetrating openings which extend perpendicularly to the waves or corrugations and each of which passes through a respective wave crest.

In one preferred embodiment, the openings are milled in the layer, and a second layer of liquid-permeable material is bonded to the wave troughs of the first layer.

Figure 2:
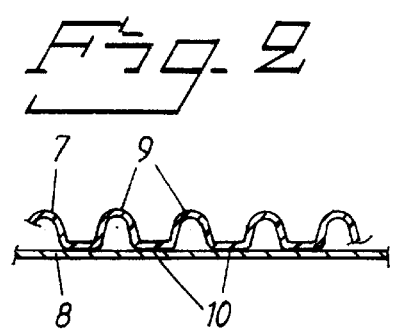
Figure 3:
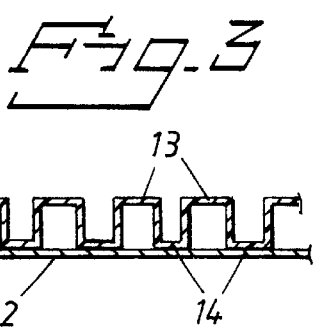
Figure 4:
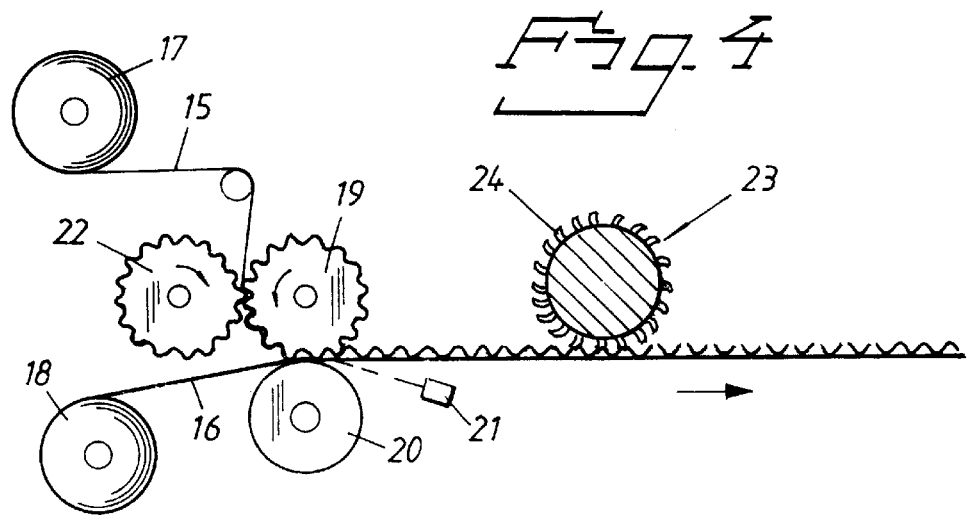

The invention will now be described with reference to the accompanying drawings, in which FIG. 1 is a schematic perspective view of part of a casing sheet according to one preferred embodiment of the invention;

FIGS. 2 and 3 are cross-sectional views of two variants of a casing sheet according to the preferred embodiment of the invention; and FIG. 4 illustrates schematically a device for manufacturing a casing sheet according to FIG. 1 in a partly sectioned side view.

The casing sheet 1 illustrated in FIG. 1 is comprised of a first corrugated or pleated layer 2 which exhibits transversely extending and mutually parallel wave-shaped folds having wave crests 3 and wave troughs 4 across the whole of its surface. A second layer 5 is suitably joined to the first layer 2, e.g. by ultrasonic welding, laser welding or by gluing.

The first layer 2 also includes longitudinally extending rows of openings 6 disposed in the crests 3 of the parallel wave-shaped corrugations.

The wave crests and wave troughs of the wave-shaped corrugations need not have the shapes shown in FIG. 1. Conceivable alternative wave shapes are shown in FIGS. 2 and 3 by way of example. The wave crests 9 of the first layer 7 shown in FIG. 2 have the same shape as the wave crests of a sinusoidal wave, whereas the wave troughs 10 have flat surfaces in abutment with the second layer 8. This configuration may be suitable in ensuring that good connection is achieved between the wave troughs 10 and the second layer 8, which may be desirable when gluing or bonding the layers 7 and 8 together, for instance. In the FIG. 3, embodiment, the mutually parallel folds in the first layer 11 have a square wave cross-sectional shape, therewith providing a maximum surface for attachment of the wave troughs 14 to the second layer 12. The wave crests 13 present flat contact surfaces to the user of an absorbent article provided with such a casing sheet. It is not essential for mutually sequential longitudinal pleats to be similar to one another and may be given mutually different wavelengths. However, the amplitude of the waves, i.e. the distance of the wave crests from the second layer, will preferably be as constant as the method of manufacture will allow, at least when seen locally. Seen globally, it may be desirable to have a greater wave amplitude within certain areas, e.g. at the wetting point of the absorbent article in which the inventive casing sheet is included, so as to generate a greater distance between the absorbent body included in an article provided with an inventive casing sheet and the wearer's skin in one particular region, therewith reducing the risk of rewetting within this region.

The first layer in the aforedescribed casing sheets is comprised of a hydrophobic (water repellant) or hydrophobized material, e.g. a plastic film, a foam material, or a hydrophobic or hydrophobized non-woven material. The reception properties of the casing sheet are determined to a great extent by the open area of the first layer and particularly the open area at the wetting point. The open area within a first layer region is determined by the number of openings in this region and the size of said openings and is given as a percentage of the area of this region. The open area will preferably be between 10 and 75%, at least within the wetting point of the article, i.e. that region of the absorbent article casing sheet within which liquid is normally delivered by a wearer.

When liquid is discharged onto a first layer according to any one of FIGS. 1–3, liquid that does not immediately enter an opening will run down into the wave troughs and there collects. For this reason, at least one of the lower edges of the openings within at least the region of the first layer that lies undermost in a donned absorbent article will preferably lie at the same distance from the second layer as the upper side of said undermost part of the wave troughs so as to prevent liquid from remaining in the wave troughs of the upper layer.

The flat, second layer of an inventive casing sheet is also liquid permeable and shall have reception properties that correspond substantially with the desired reception properties of the first layer. Because discharged liquid is able to collect in the wave troughs, as beforementioned, the reception properties of the second layer may be allowed to be somewhat poorer than otherwise desired without the casing sheet being felt to be wet, by virtue of the fact that only the wave crests of the first layer are in contact with the wearer. The second layer may be comprised of a plastic net, a perforated plastic film, a hydrophilic non-woven or a hydrophobic non-woven material having a sufficient open area, or a perforated hydrophobic nonwoven material.

An inventive casing sheet also provides good rewetting properties to an absorbent article provided with such a casing sheet, since the user contacting surface will be located relatively far from the wearer.

The wave-shaped corrugations of the first layer will suitably extend transversely across the full width of the article in which said layer is included. This allows ambient air to circulate freely and therewith ventilate the wearer's skin within the region of a donned absorbent article. Perspiration and the like can thereby be ventilated away from the skin, giving the wearer an extra feeling of dryness in comparison with an article having a flat wearer abutment surface. Small quantities of liquid present on the surface of the first layer can also be ventilated away, eg. small quantities of liquid remaining in the wave troughs.

The inventive casing sheet also provides good security against leakage due to liquid running from the article, since liquid can not readily flow past the wave troughs. Further, solids which may be present in menstrual fluid can easily be trapped in the wave troughs of the first layer. This also applies to discharged excretion when using such a casing layer in diapers.

FIG. 4 illustrates schematically an arrangement for manufacturing an inventive casing sheet from two webs of material 15, 16 stored on storage reels 17 and 18 respectively. The webs are mutually joined in a device that includes two rotatable cylinders 19, 20, for instance by causing a laser beam from a laser source 21 to fall intermittently on the nip between the cylinders 19, 20 and therewith produce a weld joint.

The web 15 may be comprised of polyethylene film and the web 16 comprised of polypropylene-based nonwoven material.

Prior to its entry into the nip defined between the cylinders 19, 20, the web 15 is pleated or corrugated between the cylinder 19 and a further cylinder 22, these cylinders having undulating peripheral surfaces which mutually engage one another in the manner of two mutually coacting toothed wheels. Subsequent to their passage through the cylinders 19, 20, the composite web comprising said webs 15, 16 will consist of an upper corrugated web 15 whose wave troughs are joined to an underlying flat web 16.

It is pointed out in this context that the laser source generates a row of laser rays which are incident to the nip between the cylinders 19, 20 in a direction at right angles to the plane of the paper in FIG. 4. The laser source used may be of the kind described in Swedish Patent Application No. 9600096-3, filed on Jan. 11, 1996. Naturally, other methods of joining the webs 15, 16 together are conceivable within the scope of the invention. For instance, the apparatus may include a glue applicator which coats the web 16 with glue or applies transversal glue strings prior to the web passing through the cylinders 19, 20. Alternatively, the web 16 may be heated prior to entering the nip between the cylinders 19, 20, e.g. by incorporating a heat source in the cylinder 20.

The composite web is thereafter passed through a milling cylinder 23 which has a plurality of axially separated rows of peripherally extending cutters 24. When passing the milling cylinder 23 longitudinally extending rows of openings corresponding to the rows of cutters 24 will be cut out of the composite web. The cylinder 23 is suitably set so that the depth of cut will be smaller than the height of the wave-shaped web 15, such as to ensure that no material will be cut from the other web 16. However, the cutting depth may be conceivably be set so that through-penetrating openings or partially penetrating openings are cut from the underlying web 16, for instance when this web is comprised of imperforate plastic film or when the reception properties of said web material need to be improved for some reason or other.

Subsequent to passage by the milling cylinder 23, individual casing sheets are cut from the composite web in a suitable manner, not shown.

An inventive casing sheet can thus be produced in a very simple way and its reception properties can be readily changed by altering the cutting depth of the miller or replacing the milling tool, therewith enabling the dimensions of individual openings and the number of rows of openings to be readily varied. The wetting properties of the casing sheet can also be readily altered, by varying the peripheral speed of the cylinders 22 and the undulating wave shape of the peripheral surface of the cylinder 19. Because the corrugations, or wave shapes, and the openings are formed by mechanical means, the corrugated layer will not be deformed plastically, meaning that the thickness of layers included in the casing sheet will not be changed in the manufacturing process and enables the strength properties of the casing sheet to be predicted more readily.

It will be understood that the described and illustrated embodiments can be modified within the scope of the invention. For instance, the second layer may comprise the upper surface of the absorbent body of an absorbent article which includes an inventive casing sheet, provided that the absorbent body is sufficiently well-bonded. Furthermore, the first layer may be provided with openings prior to being pleated, although this is not preferred for reasons of a manufacturing/technical reason. The invention is therefore solely restricted by the contents of the following claims.

I claim:

1. A liquid permeable casing sheet for absorbent sanitary articles, including:

a first layer which is corrugated over at least a central part of its surface so as to provide rows of parallel waves having wave crests and wave troughs, the wave crests forming an article contact surface with a wearer's body when the article is in use, wherein the first layer further includes through-penetrating openings arranged in parallel rows, said parallel rows of openings extending perpendicularly to said parallel rows of waves or corrugations, each of said through-penetrating openings passing through one of the wave crests; and a second layer of liquid-permeable material which is attached to the wave troughs of the first layer.

2. A method of producing a liquid-permeable casing sheet for absorbent sanitary articles, said method comprising:

corrugating or pleating a first layer to present a row of parallel waves having wave crests and wave troughs, and forming in the first layer a plurality of rows of through-penetrating openings which extend perpendicularly to the corrugations or waves, each of the openings passing through a respective wave crest; and attaching a second layer of liquid-permeable material to the wave troughs of the first layer.

3. A liquid-permeable casing sheet for use in absorbent sanitary articles, said casing sheet comprising:

a first layer corrugated over at least a central part of its surface, said corrugation providing rows of parallel waves defined by wave crests and wave troughs, the wave crests forming a contact surface with a wearer's body when the article is in use, a plurality of through-penetrating openings formed in said first layer, said openings being arranged in parallel rows which extend perpendicularly to the parallel rows of waves, and a second layer of liquid-permeable material attached to the wave troughs formed in the first layer;

wherein each of said plurality of through-penetrating openings passes through one of the wave crests.

\* \* \* \* \*